US011203568B2

(12) United States Patent
Xu et al.

(10) Patent No.: US 11,203,568 B2
(45) Date of Patent: Dec. 21, 2021

(54) METHODS OF REDUCING COLOR IN ALKANOLAMINE COMPOSITIONS AND COMPOSITIONS PRODUCED THEREBY

(71) Applicant: SABIC Global Technologies B.V., Bergen op Zoom (NL)

(72) Inventors: Feng Xu, Riyadh (SA); Flaiyh Al-Anazi, Riyadh (SA)

(73) Assignee: SABIC GLOBAL TECHNOLOGIES B.V., Bergen op Zoom (NL)

(*) Notice: Subject to any disclaimer, the term of this patent is extended or adjusted under 35 U.S.C. 154(b) by 0 days.

(21) Appl. No.: 16/062,385

(22) PCT Filed: Dec. 23, 2016

(86) PCT No.: PCT/IB2016/057983
§ 371 (c)(1),
(2) Date: Jun. 14, 2018

(87) PCT Pub. No.: WO2017/115256
PCT Pub. Date: Jul. 6, 2017

(65) Prior Publication Data
US 2018/0370899 A1     Dec. 27, 2018

Related U.S. Application Data

(60) Provisional application No. 62/272,212, filed on Dec. 29, 2015.

(51) Int. Cl.
*C07C 213/10* (2006.01)
*C07C 215/12* (2006.01)
*C01B 35/04* (2006.01)
*C01D 1/04* (2006.01)

(52) U.S. Cl.
CPC .......... *C07C 213/10* (2013.01); *C01B 35/04* (2013.01); *C01D 1/04* (2013.01); *C07C 215/12* (2013.01)

(58) Field of Classification Search
None
See application file for complete search history.

(56) References Cited

U.S. PATENT DOCUMENTS

| 2,901,513 | A  | 8/1959  | Thomas          |
|-----------|----|---------|-----------------|
| 3,159,276 | A  | 12/1964 | Moore           |
| 3,207,790 | A  | 9/1965  | Glew et al.     |
| 3,922,306 | A  | 11/1975 | Takaku et al.   |
| 4,567,303 | A  | 1/1986  | Boettger et al. |
| 4,673,762 | A  | 6/1987  | Paslean et al.  |
| 5,208,377 | A  | 5/1993  | Overgaard et al.|
| 5,227,528 | A  | 7/1993  | Webster et al.  |
| 5,693,866 | A  | 12/1997 | Roling et al.   |
| 5,847,221 | A* | 12/1998 | Gibson ............... C07C 213/10 564/498 |
| RE36,115  | E  | 3/1999  | Sullivan        |
| 6,323,371 | B2 | 11/2001 | Ruider et al.   |
| 7,164,044 | B2 | 1/2007  | Morishita et al.|
| 7,550,632 | B2 | 6/2009  | Haese et al.    |
| 8,466,323 | B2 | 6/2013  | Melder et al.   |
| 2001/0031897 | A1 | 10/2001 | Ruider et al. |
| 2004/0127748 | A1 | 7/2004  | Brun-Buisson et al. |
| 2007/0027056 | A1 | 2/2007  | Wang et al.   |
| 2014/0061020 | A1 | 3/2014  | Schmidt et al.|

FOREIGN PATENT DOCUMENTS

| CA | 2061718 A1  | 11/1992 |
| CA | 2540246 A1  | 4/2005  |
| CN | 1106792 A   | 8/1995  |
| CN | 201524433   | 7/2010  |
| EP | 0477593 A1  | 4/1992  |
| GB | 1363994 A   | 8/1974  |
| JP | 59025355 A  | 2/1984  |
| RU | 2430085 C1  | 9/2011  |

OTHER PUBLICATIONS

"Colour Inhibitor for Ethanolamines Plants", Research Disclosure, Jun. 2004, p. 724, Publication 482006 (1 page).
Wolfe, W., "Uber nichtgilbendes Triathoanolamin und seine Verwendung in derTechnik", Fette Und Seifen, 1952, 54, p. 142-143,(English translation of Title and one sentence summary of relevance.).
Hoffman, W.C., "Corrosion inhibitor for Ethanolamines Plants", Electronic Publicaton: Jun. 26, 2002, IP.COM; IP.com No. IPCOM000008614D; 2 Pages.
International Search Report for international Application No. PCT/IB2016/057983; International filing date Dec. 23, 2016; dated Mar. 17, 2017; 6 pages.
Written Opinion of the International Searching Authority for International Application No. PCT/IB2016/057983; International Filing Date: Dec. 23, 2016; dated Mar. 17, 2017; 7 pages.
Author anonymous. "Decoloration and deodorization with borohydride." Inorganic Chemicals Industry. Dec. 31, 1983. p. 38. English Translation.
Li, Wang. "Study on the Electrochemical Behavior of Coin n Hydrogenation." College of Chemistry and Chemical Engineering, Chongqing University. Master Degree Thesis of Chongqing University. Chinese Master's Theses Full-text Database, Engineering Science and Technology II. Apr. 2007. p. 19.

\* cited by examiner

Primary Examiner — Sudhakar Katakam
Assistant Examiner — Jennifer C Sawyer
(74) Attorney, Agent, or Firm — Norton Rose Fulbright US LLP

(57) ABSTRACT

A method of reducing color in an alkanolamine, the method comprising: contacting the alkanolamine with an amount of an aqueous solution effective to provide 5 to 1000 parts per million by weight of an alkali metal borohydride, based on parts by weight of the alkanolamine; and 0.5 to 10,000 parts per million by weight of an alkali metal hydroxide, based on parts by weight of the alkanolamine; preferably wherein the color-reduced alkanolamine is not distilled after the contacting.

3 Claims, No Drawings

METHODS OF REDUCING COLOR IN ALKANOLAMINE COMPOSITIONS AND COMPOSITIONS PRODUCED THEREBY

CROSS REFERENCE TO RELATED APPLICATIONS

This application is a National Stage application of International Application No. PCT/IB2016/057983, filed Dec. 23, 2016, which claims the benefit of U.S. Provisional Patent Application No. 62/272,212 filed on Dec. 29, 2015, each of which is incorporated by reference in its entirety herein.

BACKGROUND

This disclosure relates to methods of reducing color in alkanolamine compositions and the color-reduced compositions produced thereby.

Alkanolamines such as triethanolamine are used primarily as emulsifiers and surfactants in a wide variety of industrial and consumer product applications. Such applications include household goods, for example dishwashing liquids, detergents, cleaners, polishes, cement production, cosmetics such as personal care products including shaving creams, medicine, printing, metalworking fluids, paints, lubricants, and electroless plating, to name a few. A key property to assess the quality (and thus value) of pure alkanolamines such as triethanolamine is color. In general, the less color, the higher its value. Thus, alkanolamine producers commonly have two objectives in providing pure alkanolamines: inhibiting color formation, and reducing color in discolored alkanolamines. Both of these objectives are referred to herein as "reducing color."

Fractional distillation of crude alkanolamines such as triethanolamine can readily produce a pure product that is initially colorless or near colorless. Such initially colorless product, however, can gradually develop color during storage, even upon storage in sealed containers in the dark. This color development can include initial pinking, followed by yellowing, cumulative yellowing, and further darkening to the extent of eventual formation of a brown color. Discoloration is even more rapid if the alkanolamine is exposed to light. The phenomenon of alkanolamines such as triethanolamine and other ethanolamines turning color is described, for example, in "SRI International, Process Economics Program Report no. 193" of January 1991, pp. 6-9 and 6-10.

Various methods to reduce color in triethanolamine have generally not been entirely satisfactory for various reasons. A number of methods suffer from the drawback that they do not sufficiently remove color from discolored triethanolamine to the extent desired to give a colorless or near colorless product. Other methods can reduce color but cannot maintain a color-free product after color removal for a desired period of time. Moreover, certain methods to reduce color in triethanolamine have recently raised environmental and health concerns.

Some techniques for reducing color in alkanolamines such as triethanolamine require two-stage vacuum distillation as described in U.S. Pat. No. 7,164,044; use of a rectifying device as described in CN201524433U; use of a two-serial mixing and displacement apparatus as described in RU2430085C1; using a device for continuous manufacture and separation of triethanolamine as described in US2004/0127748A1; use of equipment made from substantially nickel-free alloy steel as described in U.S. Pat. No. 4,567,303; use of dividing wall columns as described in US2014/0061020A1 and CA2540246A1; use of a device comprising a distillation column and a downstream column as described in U.S. Pat. No. 8,466,323; as well as use of electromagnetic radiation, third column distillation, and short path and thin film evaporators. Disadvantages associated with these techniques include high investment cost for special equipment, cost for disposal of spent reagent after its use, as well as handling of hazardous materials.

There accordingly remains a need in the art for methods of reducing color in alkanolamines such as triethanolamine, for maintaining reduced color in alkanolamines, as well as such color-reduced compositions.

SUMMARY

In an embodiment, a method of reducing color in an alkanolamine comprises contacting the alkanolamine with an amount of an aqueous solution effective to provide 5 to 1000 parts per million by weight of an alkali metal borohydride, based on parts by weight of the alkanolamine; and 0.5 to 10,000 parts per million by weight of an alkali metal hydroxide, based on parts by weight of the alkanolamine, preferably wherein the contacted alkanolamine is not further distilled.

Also disclosed herein is a color-reduced alkanolamine composition comprising in combination: an alkanolamine, and an aqueous solution in an amount effective to provide 5 to 1000 parts per million by weight of an alkali metal borohydride, based on parts by weight of the alkanolamine; and 0.5 to 10,000 parts per million by weight of an alkali metal hydroxide, based on parts by weight of the alkanolamine, preferably wherein the color-reduced alkanolamine composition has not been distilled after manufacture of the alkanolamine.

The above described and other features are exemplified by the following detailed description.

DETAILED DESCRIPTION

As described above, unacceptable levels of color and color bodies can be found even in finished, purified alkanolamines Additionally, color bodies can form as contaminants over a period of time, for example during storage. The inventors hereof have discovered methods of reducing color in alkanolamines, or maintaining reduced color in alkanolamines. The alkanolamine is contacted with an aqueous solution of an alkali metal borohydride and an alkali metal hydroxide, to provide color-reduced alkanolamine compositions. For example, the color value of the triethanolamine can be reduced from an initial Pt-Co color value of 23 to a Pt-Co color value of 5 using these methods. In an advantageous and surprising feature, the alkanolamine as manufactured can be contacted, not subsequently distilled, and still maintain excellent color.

Advantageously, after contacting, these alkanolamine compositions are colorless or near colorless to the human eye. The compositions have a Platinum-Cobalt Color Value of less than 50, or less than 30, or 0 to 20, as determined according to Test Method ASTM D1209. In an especially advantageous feature, the low color can be maintained over months or years. Thus, in compositions treated to reduce color, or already having reduced color, the method can be used to maintain the low color over time. In another advantageous feature, the method is fast, and does not require expensive or time-consuming equipment. The color-reduced compositions can be stored, directly packaged, or transported, for example.

Further advantageously, an aqueous solution of alkali metal borohydride and alkali metal hydroxide can effectively reduce the color of triethanolamine, as determined according to Test Method ASTM D1209, in a very short amount of time. For example, six hours after an aqueous solution of an alkali metal borohydride and an alkali metal hydroxide is added to triethanolamine, the color value of the triethanolamine can be 50%, 30%, 25%, 20% or less of the initial value, for example from an initial Pt-Co color value of 23 to a Pt-Co color value of 5, for example.

The method is effective with a wide variety of alkanolamines, which includes linear, branched or cyclic compounds having at least one primary, secondary, or tertiary amino group and at least one alkanol group. Such alkanolamines include a mono($C_{1-10}$ alkanol)amine, a di($C_{1-10}$ alkanol)amine, a tri($C_{1-10}$ alkanol)amine, an N-($C_{1-10}$ alkyl) mono($C_{2-4}$ alkanol)amine, an N-($C_{1-10}$ alkyl) di($C_{2-4}$ alkanol)amine, an N,N-di($C_{1-10}$ alkyl) ($C_{2-4}$ alkanol)amine, an N-($C_{1-10}$ alkanol)pyrrolidine, an N-($C_{1-10}$ alkanol)imidazolidine, an N-($C_{1-10}$ alkanol)piperidine, or an N-($C_{1-10}$ alkanol) piperazine. In some embodiments, the alkanolamine is a mono($C_{1-4}$ alkanol)amine, a di($C_{1-4}$ alkanol)amine, a tri ($C_{1-4}$ alkanol)amine, an N-($C_{1-4}$ alkyl) mono($C_{2-4}$ alkanol) amine, an N-($C_{1-4}$ alkyl) di($C_{1-4}$ alkanol)amine, an N,N-di ($C_{1-4}$ alkyl) ($C_{2-4}$ alkanol)amine, an N-($C_{1-4}$ alkanol) pyrrolidine, N-($C_{1-4}$ alkanol)imidazolidine, an N-($C_{1-4}$ alkanol)piperidine, or an N-($C_{1-4}$ alkanol)piperazine. Specific alkanolamines are monoethanolamine (MEA), diethanolamine (DEA), triethanolamine (TEA), methyl diethanolamine, isopropanolamine, diisopropanolamine, and (2-hydroxyethyl)piperazine. A combination comprising at least one of the foregoing alkanolamines can be used.

In some embodiments, the alkanolamine is triethanolamine. Methods for the manufacture of triethanolamine are known. For example, triethanolamine compositions can be made by a process that comprises distilling triethanolamine from a mixture that includes at least diethanolamine and triethanolamine in the presence of phosphorous acid ($H_3PO_3$). A method of preparation and distillation of triethanolamine is described in, for example, U.S. Pat. No. 6,323,371.

The alkali metal borohydride can be sodium borohydride, potassium borohydride, or lithium borohydride, but is preferably sodium borohydride or potassium borohydride. The aqueous solution can have 5 to 1000 parts per million by weight of an alkali metal borohydride, or 10 to 900 parts per million by weight of an alkali metal borohydride, or 25 to 800 parts per million by weight of an alkali metal borohydride, based on parts by weight of the alkanolamine.

The alkali metal hydroxide can be sodium hydroxide, potassium hydroxide, lithium hydroxide, rubidium hydroxide, or cesium hydroxide, but is preferably sodium hydroxide or potassium hydroxide. The aqueous solution can have 0.5 to 10,000 parts per million by weight of the alkali metal hydroxide, or 1 to 8,000 parts per million by weight of the alkali metal hydroxide, or 10 to 5,000 parts per million by weight of the alkali metal hydroxide, based on parts by weight of the alkanolamine.

When contacting the alkanolamine with the alkali metal borohydride and alkali metal hydroxide aqueous solution, the alkali metal borohydride and alkali metal hydroxide aqueous solution is present in an amount effective to reduce color. The aqueous solution can have a total of 1 to 80 weight percent, or 20 to 80 weight percent, or 30 to 70 weight percent, or 40 to 60 weight percent, of the alkali metal borohydride and the alkali metal hydroxide, based on the total weight of the aqueous solution. Other components can be present in the aqueous solution (e.g., a heat stabilizer, buffer, ultraviolet light absorber, or the like), provided that any such additive does not substantially adversely affect the color-reducing ability of the aqueous composition.

The alkanolamine compositions can have any level of color before treatment with the alkali metal borohydride and alkali metal hydroxide aqueous solution, including low, very low, or no color before treatment with the aqueous solution. As described in more detail below, treatment of alkanolamine compositions having low, very low, or no color can be to prevent color formation over time. For convenience, any alkanolamine composition treated with the alkali metal borohydride and alkali metal hydroxide aqueous solution as described herein can be referred to as a "color-reduced alkanolamine composition."

Contacting the alkanolamine with the alkali metal borohydride and alkali metal hydroxide aqueous solution can be at a temperature from 20° C. to 250° C., or 20° C. to 150° C., or 20° C. to 90° C., or 20° C. to 40° C. Lower temperatures (e.g., 20° C. to 40° C.) are preferred to prevent side reactions that can cause color. Contacting can be for a selected period of time, for example, 10 minutes to 50 hours, or 30 minutes to 30 hours, or 1 hour to 24 hours. Contacting can be by mixing of the alkanolamine and the alkali metal borohydride and alkali metal hydroxide aqueous solution, during or after the contacting. It is to be understood that the alkali metal borohydride and alkali metal hydroxide aqueous solution is generally not subsequently quenched or removed from the alkanolamine, such that the above contacting temperatures and times may simply be for an initial period before the alkanolamine is further processed, for example transported or packaged for storage or transportation.

Contacting the alkanolamine with the alkali metal borohydride and alkali metal hydroxide aqueous solution reduces initial color, e.g., color bodies and color contaminants, present in the alkanolamine before such contact, and provides the color-reduced alkanolamine compositions herein. The inventors hereof have advantageously found that such initial color is reduced during or after contacting to the extent that the resultant alkanolamine compositions are colorless or near colorless. Without wishing to be bound by any specific theory, borane is believed to be liberated during contacting and acts as a reducing agent, of any color bodies or contaminants that cause color bodies to be present in the alkanolamine.

The color-reduced alkanolamine compositions produced by the methods described herein, for example color-reduced triethanolamine compositions, can have significantly reduced or low color. For example, the Hazen color, specifically the Platinum-Cobalt Color Value as determined according to Test Method ASTM D1209 ("Pt-Co color value") can be less than 50, or less than 30. It has surprisingly been found that the Pt-Co color value can be 0 to 20.

Further advantageously, the color-reduced alkanolamine compositions produced by these methods, specifically color-reduced triethanolamine compositions, can maintain these very low color values over extended periods. The alkali metal borohydride and alkali metal hydroxide aqueous solution can thus prevent color increases over time. For example, the color-reduced alkanolamine compositions produced by the methods described herein, specifically color-reduced triethanolamine compositions, when stored at room temperature (e.g., 20° C. to 25° C.) for a period of three months to eight years, or one year to eight years, or three months to six months, or six months to one year, or one year to three years, or one year to six years, following the contacting, can have a Pt-Co color value of less than 50, or less than 30, or 0 to 20.

In some embodiments, the color-reduced alkanolamine compositions can have a Pt-Co color value of less than 50, or less than 30, or 0 to 20, after storage at room temperature (e.g., 20° C. to 25° C.) for a period of three months to eight years, or one year to eight years, or three months to six months, or six months to one year, or one year to three years, or one year to six years, following the contacting when protected from light. "Storage" as used herein includes periods where the compositions are not in active use, for example where the compositions are transported. "Protected from light" can mean that the compositions are stored under conditions where visible light is excluded for at least 90% of the time during storage.

In other embodiments, the color-reduced alkanolamine compositions produced by the methods described herein, specifically color-reduced triethanolamine compositions, can have a Pt-Co color value that does not increase by more than 4 times, or more than 3 times, or more than 2 times, when stored at room temperature (e.g., 20° C. to 25° C.) for a period of three months to eight years, or one year to eight years, or three months to six months, or six months to one year, or one year to three years, or one year to six years, following the contacting. In some embodiments, the color-reduced alkanolamine compositions produced by the methods described herein, specifically color-reduced triethanolamine compositions, can have a Pt-Co color value that does not increase by more than 4 times, or more than 3 times, or more than 2 times, when stored at room temperature (e.g., 20° C. to 25° C.) for a period of three months to eight years, or one year to eight years, or three months to six months, or six months to one year, or one year to three years, or one year to six years when protected from light.

The alkanolamine compositions produced by these methods are also color-stable at elevated temperatures. Thus, the color-reduced alkanolamine compositions produced by the methods described herein, specifically color-reduced triethanolamine compositions, when stored at 30° C. to 60° C., or 40° C. to 50° C., or 45° C., for a period of one month to six years, or one month to two years, or three months to one year, or six months following the contacting, can have a Pt-Co color value of less than 50, or less than 30, or 0 to 20, or compositions can have a Pt-Co color value of less than 50, or less than 30, or 0 to 20, after storage at 30° C. to 60° C., or 40° C. to 50° C., or 45° C., for a period of one month to six years, or one month to two years, or three months to one year, or six months following the contacting when protected from light. In other embodiments, the color-reduced alkanolamine compositions produced by the methods described herein, specifically color-reduced triethanolamine compositions, can have a Pt-Co color value that does not increase by more than 4 times, or more than 3 times, or more than 2 times, when stored at 30° C. to 60° C., or 40° C. to 50° C., or 45° C. for a period of one month to six years, or one month to two years, or three months to one year, or six months following the contacting. In some embodiments, the color-reduced alkanolamine compositions produced by the methods described herein, specifically color-reduced triethanolamine compositions, can have a Pt-Co color value that does not increase by more than 4 times, or more than 3 times, or more than 2 times, when stored at 30° C. to 60° C., or 40° C. to 50° C., or 45° C., for a period of one month to six years, or one month to two years, or three months to one year, or six months years when protected from light.

The color-reduced compositions can comprise an alkanolamine and residual materials such as unreacted alkali metal borohydride, or unreacted alkali metal hydroxide, or reaction products thereof, or degradation products. The residual materials in the color-reduced compositions can accordingly be 0.1 to 5,000 ppm, or 5 to 2,000 ppm, or 5 to 1,000 ppm.

Accordingly, color-reduced alkanolamine compositions comprising an alkanolamine and 0.1 to 5000 ppm of residual materials, or 5 to 2,000 ppm of residual materials, or 5 to 1,000 ppm of residual materials, can have a Pt-Co color value of less than 50, or less than 30. In an embodiment, the Pt-Co color value can be 0 to 20. In some embodiments, color-reduced triethanolamine compositions comprising triethanolamine and 0.1 to 5,000 ppm of residual materials, or 5 to 2,000 ppm of residual materials, or 5 to 1,000 ppm of residual materials, can have a Pt-Co color value of less than 50, or less than 30. In an embodiment, the Pt-Co color value of the color-reduced triethanolamine composition comprising residual materials can be 0 to 20.

The color-reduced alkanolamine compositions can maintain these very low color values over extended time. For example, the color-reduced alkanolamine compositions produced by these methods, specifically color-reduced triethanolamine compositions, comprising an alkanolamine and 0.1 to 5000 ppm of residual materials, or 5 to 2,000 ppm of residual materials, or 5 to 1,000 ppm of residual materials, after storage at room temperature (e.g., 20° C. to 25° C.) for a period of three months to eight years, or one year to eight years, or three months to six months, or six months to one year, or one year to three years, or one year to six years following the contacting, can have a Pt-Co color value of less than 50, or less than 30, or 0 to 20. The color-reduced alkanolamine compositions produced by these methods, specifically color-reduced triethanolamine compositions, comprising an alkanolamine and 0.1 to 5000 ppm of residual materials, or 5 to 2,000 ppm of residual materials, or 5 to 1,000 ppm of residual materials can have a Pt-Co color value of less than 50, or less than 30, or 0 to 20 after storage at room temperature (e.g., 20° C. to 25° C.) for a period of three months to eight years, or one year to eight years, or three months to six months, or six months to one year, or one year to three years, or one year to six years when the compositions are protected from light.

The color-reduced alkanolamine compositions produced by these methods, specifically color-reduced triethanolamine compositions, comprising an alkanolamine and 0.1 to 5000 ppm of residual materials, or 5 to 2,000 ppm of residual materials, or 5 to 1,000 ppm of residual materials, can have a Pt-Co color value that does not increase by more than 4 times, or more than 3 times, or more than 2 times, after storage at room temperature (e.g., 20° C. to 25° C.) for a period of three months to eight years, or one year to eight years, or three months to six months, or six months to one year, or one year to three years, or one year to six years following the contacting. The color-reduced alkanolamine compositions produced by these methods, specifically color-reduced triethanolamine compositions, comprising an alkanolamine and 0.1 to 5000 ppm of residual materials, or 5 to 2,000 ppm of residual materials, or 5 to 1,000 ppm of residual materials can have a Pt-Co color value that does not increase by more than 4 times, or more than 3 times, or more than 2 times, after storage at room temperature (e.g., 20° C. to 25° C.) for a period of three months to eight years, or one year to eight years, or three months to six months, or six months to one year, or one year to three years, or one year to six years when the compositions are protected from light.

In some embodiments, color-reduced triethanolamine compositions produced by these methods, specifically color-reduced triethanolamine compositions, comprising an alkanolamine and 0.1 to 5000 ppm of residual materials, or 5 to 2,000 ppm of residual materials, or 5 to 1,000 ppm of residual materials, after storage at 30° C. to 60° C., or 40° C. to 50° C., or 45° C. for a period of one month to six years, or one month to two years, or three months to one year, or six months following the contacting, can have a Pt-Co color value less than 50, or less than 30, or 0 to 20. The color-reduced alkanolamine compositions produced by these methods, specifically color-reduced triethanolamine compositions, comprising an alkanolamine and 0.1 to 5000 ppm of residual materials, or 5 to 2,000 ppm of residual materials, or 5 to 1,000 ppm of residual materials, triethanolamine compositions can have Pt-Co color value of less than 50, or less than 30, or 0 to 20 after storage at 30° C. to 60° C., or 40° C. to 50° C., or 45° C. for a period of one month to six years, or one month to two years, or three months to one year, or six months when the compositions are protected from light.

In other embodiments, the color-reduced alkanolamine compositions produced by the methods described herein, specifically color-reduced triethanolamine compositions comprising an alkanolamine, specifically triethanolamine and 0.1 to 4,500 ppm of residual materials, or 5 to 2,000 ppm of residual materials, or 5 to 1,000 ppm of residual materials, can have a Pt-Co color value that does not increase by more than 4 times, or more than 3 times, or more than 2 times, when stored at 30° C. to 60° C., or 40° C. to 50° C., or 45° C. for a period of one month to six years, or one month to two years, or three months to one year, or six months following the contacting. In some embodiments, the color-reduced alkanolamine compositions produced by the methods described herein, specifically color-reduced triethanolamine compositions, comprising an alkanolamine, specifically triethanolamine and 0.1 to 4,500 ppm of residual materials, or 5 to 2,000 ppm of residual materials, or 5 to 1,000 ppm of residual materials, can have a Pt-Co color value that does not increase by more than 4 times, or more than 3 times, or more than 2 times, when stored at 30° C. to 60° C., or 40° C. to 50° C., or 45° C., for a period of one month to six years, or one month to two years, or three months to one year, or six months years when protected from light.

The color-reduced alkanolamine compositions can include water. For example, water can be present in the compositions in an amount of less than 10 weight percent (wt. %), or less than 5 wt. %, or less than 3 wt. %, or less than 1 wt. %, or less than 0.5 wt. %, based on the total weight of the color-reduced alkanolamine composition.

As mentioned above, an advantage of this method is that the alkanolamine compositions do not require subsequent purification or processing, e.g., distillation, after being contacted with the alkali metal borohydride and alkali metal hydroxide aqueous solution. In particular, the color-reduced alkanolamine does not require subsequent distillation or purification to remove residual materials such as unreacted borohydrides or hydroxides, or reaction products, or degradation products. Thus, in some embodiments an as-synthesized alkanolamine can be contacted to reduce color, then not distilled or otherwise purified, and still attain low color or retain the low color after storage as described above. This can save significant time and cost in the manufacture of the alkanolamines. For example, in these embodiments, the as-synthesized alkanolamine can be contacted and packaged for storage or transport within 3 hours, within 6 hours, or within 24 hours of contacting, and without distillation. In other embodiments the as-synthesized alkanolamine is stored after synthesis before contacting, for example for at least 24 hours, at least 1 week, or at least one month. The stored compositions can then still be contacted as described above to reduce any color and provide low color on further storage.

The alkanolamine compositions can be used for virtually any purpose, for example as emulsifiers, surfactants, solvents, co-solvents, pH adjusting agents, or buffering agents, as well as in any other known uses, in a wide variety of applications. Such applications include household goods, cement production, cosmetics, medicine, printing, chemical manufacturing (e.g., as a solvent, catalyst, or reactant, and electroless plating. Some products that can include the alkanolamines include liquid laundry detergents, dishwashing liquids, general cleaners, hand cleaners, polishes, metalworking fluids, paints, shaving cream, and printing inks.

The following Examples are provided for illustrative purposes only and are not to be construed as limiting in any manner.

EXAMPLES

Color determination was carried out on a LICO 690 Colorimeter from Koehler Instrument Company in accordance with the Pt-Co test method as described in ASTM D1209 (2011). Results are reported as Pt-Co Color Values.

Example. Color Stability of a Color-Reduced Triethanolamine Composition

An aqueous solution of sodium borohydride (12%, weight percentage) and sodium hydroxide (40%, weight percentage) was prepared.

Triethanolamine (1000 g, Sigma Aldrich, 99% purity) having a Pt-Co Color Value (ASTM D1209) of 23 was mixed with the above prepared aqueous solution (1.6724 g, containing 200.7 mg sodium borohydride and 669.0 mg sodium hydroxide, equal to 200 ppm of sodium borohydride and 669 ppm of sodium hydroxide to triethanolamine) The mixture was vigorously shaken to allow the aqueous solution to be distributed homogenously in the triethanolamine Over a period of 6 hours the mixture cleared.

A sample was taken for color analysis after the mixture was cleared. It was found the color index was about 5 and found to have a Pt-Co Color value (ASTM D1209) less than 15 for 2 years at room temperature (20-25° C.).

Comparative experiments of using sodium borohydride or sodium hydroxide separately to improve the color quality of triethanolamine were performed. Neither of the single components sodium borohydride or sodium hydroxide could reduce the color of triethanolamine as effectively and continuously as the combination of sodium borohydride and sodium hydroxide.

The methods and compositions are further illustrated by the following embodiments.

Embodiment 1: A method of reducing color in an alkanolamine, the method comprising: contacting the alkanolamine with an amount of an aqueous solution effective to provide 5 to 1000 parts per million by weight of an alkali metal borohydride, based on parts by weight of the alkanolamine; and 0.5 to 10,000 parts per million by weight of an alkali metal hydroxide, based on parts by weight of the alkanolamine; preferably wherein the color-reduced alkanolamine is not distilled after the contacting.

Embodiment 2: The method of Embodiment 1, wherein the color-reduced alkanolamine is packaged for storage or transportation without distillation.

Embodiment 3: The method of Embodiment 1 or Embodiment 2, wherein the color-reduced alkanolamine has a Platinum-Cobalt Color Value, Test Method ASTM D1209, of less than 50, preferably less than 30, more preferably 0 to less than or equal to 20.

Embodiment 4: The method of any one or more of Embodiments 1 to 3, wherein the alkanolamine is a mono($C_{1-10}$ alkanol)amine, a di($C_{1-10}$ alkanol)amine, a tri($C_{1-10}$ alkanol)amine, an N-($C_{1-10}$ alkyl) mono($C_{2-4}$ alkanol)amine, an N-($C_{1-10}$ alkyl) di($C_{2-4}$ alkanol)amine, an N,N-di($C_{1-10}$ alkyl) ($C_{2-4}$ alkanol)amine, an N-($C_{1-10}$ alkanol)pyrrolidine, an N-($C_{1-10}$ alkanol) imidazolidine, an N-($C_{1-10}$ alkanol) piperidine, an N-($C_{1-10}$ alkanol)piperazine, or a combination comprising at least one of the foregoing; preferably monoethanolamine, diethanolamine, triethanolamine, methyldiethanolamine, isopropanolamine, diisopropanolamine, (2-hydroxyethyl)piperazine, or a combination comprising at least one of the foregoing.

Embodiment 5: The method of any one or more of Embodiments 1 to 4, wherein the alkanolamine is a tri($C_{1-10}$ alkanol)amine, preferably triethanolamine.

Embodiment 6: The method of any one or more of Embodiments 1 to 5, wherein the aqueous solution comprises a total of 20 to 80 weight percent, or 30 to 70 weight percent, or 40 to 60 weight percent, of the alkali metal borohydride and the alkali metal hydroxide, based on the total weight of the aqueous solution.

Embodiment 7: The method of any one or more of Embodiments 1 to 6, wherein the alkali metal borohydride is sodium borohydride or potassium borohydride, and the alkali metal hydroxide is sodium hydroxide or potassium hydroxide.

Embodiment 8: The method of any one or more of Embodiments 1 to 7, wherein contacting is with 10 to 900, or 25 to 800 parts per million by weight of the alkali metal borohydride, based on parts by weight of the alkanolamine; and 1 to 8,000, or 10 to 5,000 parts per million by weight of the alkali metal hydroxide, based on parts by weight of the alkanolamine.

Embodiment 9: The method of any one or more of Embodiments 1 to 8, comprising less than 5 wt % of water, preferably less than 1 wt % of water, based on the total weight of the triethanolamine.

Embodiment 10: The method of any one or more of Embodiments 1 to 9, further comprising storing the color-reduced composition.

Embodiment 11: A color-reduced alkanolamine composition, the composition, comprising in combination: an alkanolamine, and an aqueous solution in an amount effective to provide 5 to 1000 parts per million by weight of an alkali metal borohydride, based on parts by weight of the alkanolamine; and 0.5 to 10,000 parts per million by weight of an alkali metal hydroxide, based on parts by weight of the alkanolamine.

Embodiment 12: The composition of Embodiment 11, wherein the composition has a Platinum-Cobalt Color Value, Test Method ASTM D1209, of less than 50, preferably less than 30, more preferably 0 to less than or equal to 20.

Embodiment 13: The composition of Embodiment 11 or 12, wherein the Platinum-Cobalt Color Value, Test Method ASTM D1209, does not increase by more than more than 4 times, or more than 3 times, or more than 2 times, for a period of six months to one year, or one to two years, or one to three years after storage at room temperature.

Embodiment 14: The composition of Embodiment 11 or 12, wherein the Platinum-Cobalt Color Value, Test Method ASTM D1209, does not increase by more than 4 times for a period of three to six months, or six months to one year, or one to two years, or one to three years after storage at 30° C. to 60° C., or 40° C. to 50° C.

Embodiment 15: The composition of any one or more of Embodiments 11 to 14, wherein the alkanolamine is a mono($C_{1-10}$ alkanol)amine, a di($C_{1-10}$ alkanol)amine, a tri ($C_{1-10}$ alkanol)amine, an N—($C_{1-10}$ alkyl) mono($C_{2-4}$ alkanol)amine, an N—($C_{1-10}$ alkyl) di($C_{2-4}$ alkanol)amine, an N,N-di($C_{1-10}$ alkyl) ($C_{2-4}$ alkanol)amine, an N—($C_{1-10}$ alkanol)pyrrolidine, an N—($C_{1-10}$ alkanol) imidazolidine, an N—($C_{1-10}$ alkanol)piperidine, an N—($C_{1-10}$ alkanol)piperazine, or a combination comprising at least one of the foregoing; preferably monoethanolamine, diethanolamine, triethanolamine, methyldiethanolamine, isopropanolamine, diisopropanolamine, (2-hydroxyethyl)piperazine, or a combination comprising at least one of the foregoing.

Embodiment 16: The composition of any one or more of Embodiments 11 to 15, wherein the alkanolamine is a tri($C_{1-10}$ alkanol)amine, preferably triethanolamine.

Embodiment 17: The composition of any one or more of Embodiments 11 to 16, wherein the aqueous solution comprises a total of 20 to 80 weight percent, or 30 to 70 weight percent, or 40 to 60 weight percent, of the alkali metal borohydride and the alkali metal hydroxide, based on the total weight of the solution.

Embodiment 18: The composition of any one or more of Embodiments 11 to 17, wherein the alkali metal borohydride is sodium borohydride or potassium borohydride, and the alkali metal hydroxide is sodium hydroxide or potassium hydroxide.

Embodiment 19: The composition of any one or more of Embodiments 11 to 18, wherein contacting is with 10 to 900, or 25 to 800 parts per million by weight of the alkali metal borohydride, based on parts by weight of the alkanolamine; and 1 to 8,000, or 10 to 5,000 parts per million by weight of the alkali metal hydroxide, based on parts by weight of the alkanolamine.

Embodiment 20: The composition of any one or more of Embodiments 11 to 19, comprising less than 5 wt % of water, preferably less than 1 wt % of water, based on the total weight of the triethanolamine.

In general, the methods and compositions can alternatively comprise, consist of, or consist essentially of, any appropriate steps or components herein disclosed. The methods or compositions can additionally, or alternatively, be formulated so as to be devoid, or substantially free, of any steps, components, materials, ingredients, adjuvants or species used in the prior art compositions or that are otherwise not necessary to the achievement of the function and/or objectives described herein.

The singular forms "a," "an," and "the" include plural referents unless the context clearly dictates otherwise. "Or" means "and/or." The endpoints of all ranges directed to the same component or property are inclusive and independently combinable. Disclosure of a narrower range or more specific group in addition to a broader range is not a disclaimer of the broader range or larger group. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

As used herein, the term "hydrocarbyl" includes groups containing carbon, hydrogen, and optionally one or more heteroatoms (e.g., 1, 2, 3, or 4 atoms such as halogen, O, N, S, P, or Si). "Alkyl" means a branched or straight chain, saturated, monovalent hydrocarbon group, e.g., methyl, ethyl, i-propyl, and n-butyl. "Alkylene" means a straight or branched chain, saturated, divalent hydrocarbon group (e.g., methylene (—$CH_2$—) or propylene (—$(CH_2)_3$—)). "Alkenyl" and "alkenylene" mean a monovalent or divalent, respectively, straight or branched chain hydrocarbon group having at least one carbon-carbon double bond (e.g., ethenyl (—HC=$CH_2$) or propenylene (—HC($CH_3$)=$CH_2$—). "Alkynyl" means a straight or branched chain, monovalent hydrocarbon group having at least one carbon-carbon triple bond (e.g., ethynyl). "Alkoxy" means an alkyl group linked via an oxygen (i.e., alkyl-O—), for example methoxy, ethoxy, and sec-butyloxy. "Cycloalkyl" and "cycloalkylene" mean a monovalent and divalent cyclic hydrocarbon group, respectively, of the formula —$C_nH_{2n-x}$ and —$C_nH_{2n-2x}$— wherein x is the number of cyclization(s) and n is an integer representing normal valence, for example from 3 to 8. "Aryl" means a monovalent, monocyclic or polycyclic, aromatic group (e.g., phenyl or naphthyl). "Arylene" means a divalent, monocyclic or polycyclic, aromatic group (e.g., phenylene or naphthylene). The prefix "halo" means a group or compound including one more halogen (F, Cl, Br, or I) substituents, which can be the same or different. The prefix "hetero" means a group or compound that includes at least one ring member that is a heteroatom (e.g., 1, 2, or 3) heteroatoms, wherein each heteroatom is independently the same or different and is N, O, S, or P.

"Substituted" means that the compound or group is substituted with at least one (e.g., 1, 2, 3, or 4) substituents instead of hydrogen, where each substituent is independently the same or different and is nitro (—$NO_2$), cyano (—CN), hydroxy (—OH), halogen, thiol (—SH), thiocyano (—SCN), $C_{1-6}$ alkyl, $C_{2-6}$ alkenyl, $C_{2-6}$ alkynyl, $C_{1-6}$ haloalkyl, $C_{1-9}$ alkoxy, $C_{1-6}$ haloalkoxy, $C_{3-12}$ cycloalkyl, $C_{5-18}$ cycloalkenyl, $C_{6-12}$ aryl, $C_{7-13}$ arylalkylene (e.g., benzyl), $C_{7-12}$ alkylarylene (e.g., toluyl), $C_{4-12}$ heterocycloalkyl, $C_{3-12}$ heteroaryl, $C_{1-6}$ alkyl sulfonyl (—S(=O)$_2$-alkyl), $C_{6-12}$ arylsulfonyl (—S(=O)2-aryl), or tosyl ($CH_3C_6H_4SO_2$—), provided that the substituted atom's normal valence is not exceeded, and that the substitution does not significantly adversely affect the manufacture, stability, or desired property of the compound. When a compound is substituted, the indicated number of carbon atoms is the total number of carbon atoms in the group, including those of the substituent(s).

While the invention has been described with reference to an exemplary embodiment or embodiments, it will be understood by those skilled in the art that various changes can be made and equivalents can be substituted for elements thereof without departing from the scope of the invention. In addition, many modifications can be made to adapt a particular situation or material to the teachings of the invention without departing from the essential scope thereof.

The invention claimed is:

1. A color-reduced alkanolamine composition comprising:
water;
an alkanolamine;
from 10 to 900 parts per million by weight of an alkali metal borohydride, based on parts by weight of the alkanolamine, wherein the alkali metal borohydride is potassium borohydride;
1 to 8,000 parts per million by weight of an alkali metal hydroxide, based on parts by weight of the alkanolamine, wherein the alkali metal hydroxide is potassium hydroxide; and
from 0.1 to 5000 parts per million of residual materials;
wherein the alkanolamine is selected from the group consisting of an N—($C_{1-10}$ alkyl) di($C_1$ alkanol)amine, and triethanolamine, and wherein the composition comprises less than 5 wt % of the water, based on the total weight of the triethanolamine, or a combination comprising at least one of the foregoing;
wherein the composition has a Platinum-Cobalt Color Value, Test Method ASTM D1209, of 0 to less than 15; and
wherein the Platinum-Cobalt Color Value, Test Method ASTM D1209, does not increase in value by more than more than 4 times for a period of six months to one year, or one to two years, or one to three years after storage at room temperature.

2. The composition of claim 1, wherein the alkanolamine is triethanolamine.

3. The composition of claim 1 containing 200 ppm potassium borohydride and 669 ppm potassium hydroxide.

* * * * *